(12) United States Patent
Bar-Shalev et al.

(10) Patent No.: US 9,058,665 B2
(45) Date of Patent: Jun. 16, 2015

(54) SYSTEMS AND METHODS FOR IDENTIFYING BONE MARROW IN MEDICAL IMAGES

(75) Inventors: Avi Bar-Shalev, Kiryat Haim (IL); Ravindra Mohan Manjeshwar, Glenville, NY (US)

(73) Assignee: General Electric Company, Schenectady, NY (US)

( * ) Notice: Subject to any disclaimer, the term of this patent is extended or adjusted under 35 U.S.C. 154(b) by 836 days.

(21) Appl. No.: 12/650,036

(22) Filed: Dec. 30, 2009

(65) Prior Publication Data

US 2011/0158494 A1 Jun. 30, 2011

(51) Int. Cl.
*G06K 9/00* (2006.01)
*G06T 7/00* (2006.01)
*A61B 6/03* (2006.01)
*A61B 6/00* (2006.01)

(52) U.S. Cl.
CPC .............. *G06T 7/0081* (2013.01); *A61B 6/032* (2013.01); *A61B 6/505* (2013.01); *G06T 7/0012* (2013.01); *G06T 2207/10081* (2013.01); *G06T 2207/20141* (2013.01); *G06T 2207/30008* (2013.01); *A61B 6/508* (2013.01)

(58) Field of Classification Search
CPC ................... G06T 7/0012; G06T 2207/10072; G06T 7/0081
USPC .................................................. 382/128–132
See application file for complete search history.

(56) References Cited

U.S. PATENT DOCUMENTS

| 6,021,213 | A | 2/2000 | Helterbrand et al. |
| 6,173,083 | B1 * | 1/2001 | Avinash .................. 382/260 |
| 6,463,168 | B1 * | 10/2002 | Alyassin et al. .............. 382/131 |
| 2003/0035773 | A1 | 2/2003 | Sofia Totterman et al. |
| 2003/0036083 | A1 | 2/2003 | Tamez-Pena et al. |

(Continued)

FOREIGN PATENT DOCUMENTS

| EP | 0803843 A2 | 10/1997 |
| WO | 2009/067680 A1 | 5/2009 |

OTHER PUBLICATIONS

Senseney et al. "Automated segmentation of computed tomography images", Computer-Based Medical Systems, 2009. CBMS 2009. 22nd IEEE International Symposium on, pp. 1-7, Aug. 2-5, 2009 doi: 10.1109/CBMS.2009.5255342.*

(Continued)

*Primary Examiner* — Mark Holcomb
*Assistant Examiner* — Jonathan K Ng
(74) *Attorney, Agent, or Firm* — Dean D. Small; The Small Patent Law Group, LLC

(57) ABSTRACT

Systems and method for identifying bone marrow in medical images are provided. A method includes obtaining a three-dimensional (3D) computed tomography (CT) volume data set corresponding to an imaged volume and identifying voxels in the 3D CT volume data set having a Hounsfield Unit (HU) value below a bone threshold. The voxels are identified without using image continuity. The method further includes marking the identified voxels as non-bone voxels, determining definite tissue voxels based on the identified non-bone voxels and expanding a region defined by the definite tissue voxels. The method also includes segmenting the expanded region to identify bone voxels and bone marrow voxels and identifying bone marrow as voxels that are not the bone voxels.

13 Claims, 22 Drawing Sheets

(56) References Cited

U.S. PATENT DOCUMENTS

| | | | |
|---|---|---|---|
| 2004/0101183 A1* | 5/2004 | Mullick et al. | 382/131 |
| 2005/0010106 A1* | 1/2005 | Lang et al. | 600/425 |
| 2005/0113663 A1 | 5/2005 | Tamez-Pena et al. | |
| 2005/0157925 A1* | 7/2005 | Lorenz | 382/173 |
| 2006/0239519 A1 | 10/2006 | Nowinski et al. | |
| 2007/0019850 A1* | 1/2007 | Knoplioch et al. | 382/131 |
| 2007/0055136 A1 | 3/2007 | Yamamoto et al. | |
| 2007/0116332 A1 | 5/2007 | Cai et al. | |
| 2007/0165923 A1 | 7/2007 | Shen et al. | |
| 2008/0049999 A1 | 2/2008 | Jerebko et al. | |
| 2010/0254588 A1* | 10/2010 | Cualing et al. | 382/133 |
| 2011/0002523 A1* | 1/2011 | Prakash et al. | 382/131 |
| 2011/0142316 A1* | 6/2011 | Wang et al. | 382/131 |
| 2013/0236076 A1* | 9/2013 | Averbuch et al. | 382/131 |

OTHER PUBLICATIONS

Kramer et al. "All about MAX: a male adult voxel phantom for Monte Carlo calculations in radiation protection dosimetry", R Kramer et al 2003 Phys. Med. Biol. 48 1239.*

Lark, "Cone beam technology: a brief technical overview", www.dentaleconomics.com, 2008.*

Cunningham, "Computed Tomography", The Biomedical ENgineering Handbook: Second Edition, 2000.*

Buie et al. "Automatic segmentation of cortical and trabecular compartments based on a dual threshold technique for in vivo micro-CT bone analysis.", Bone. Oct. 2007;41(4):505-15. Epub Jul. 18, 2007.*

Partial International Search from corresponding PCT Application No. PCT/US2010/060274 on Apr. 11, 2011.

Shen, et al. "Improved Prediction of Myelotoxicity using a Patient-Specific Imaging Dose Estimated for Non-Marrow-Targeting 90Y-Antibody Therapy", Journal of Nuclear Medicine, vol. 43, No. 9, Sep. 2002, pp. 1245-1253.

Hasegawa, et al. "Automated Extraction of Lung Cancer Lesions from Multislice Chest CT Images by Using Three-Dimensional Image Processing", Systems & Computers in Japan, vol. 25, No. 11, Oct. 1, 1994, pp. 68-76.

International Search Report and Written Opinion from corresponding PCT Application No. PCT/US2010/060274 on Jun. 20, 2011.

* cited by examiner

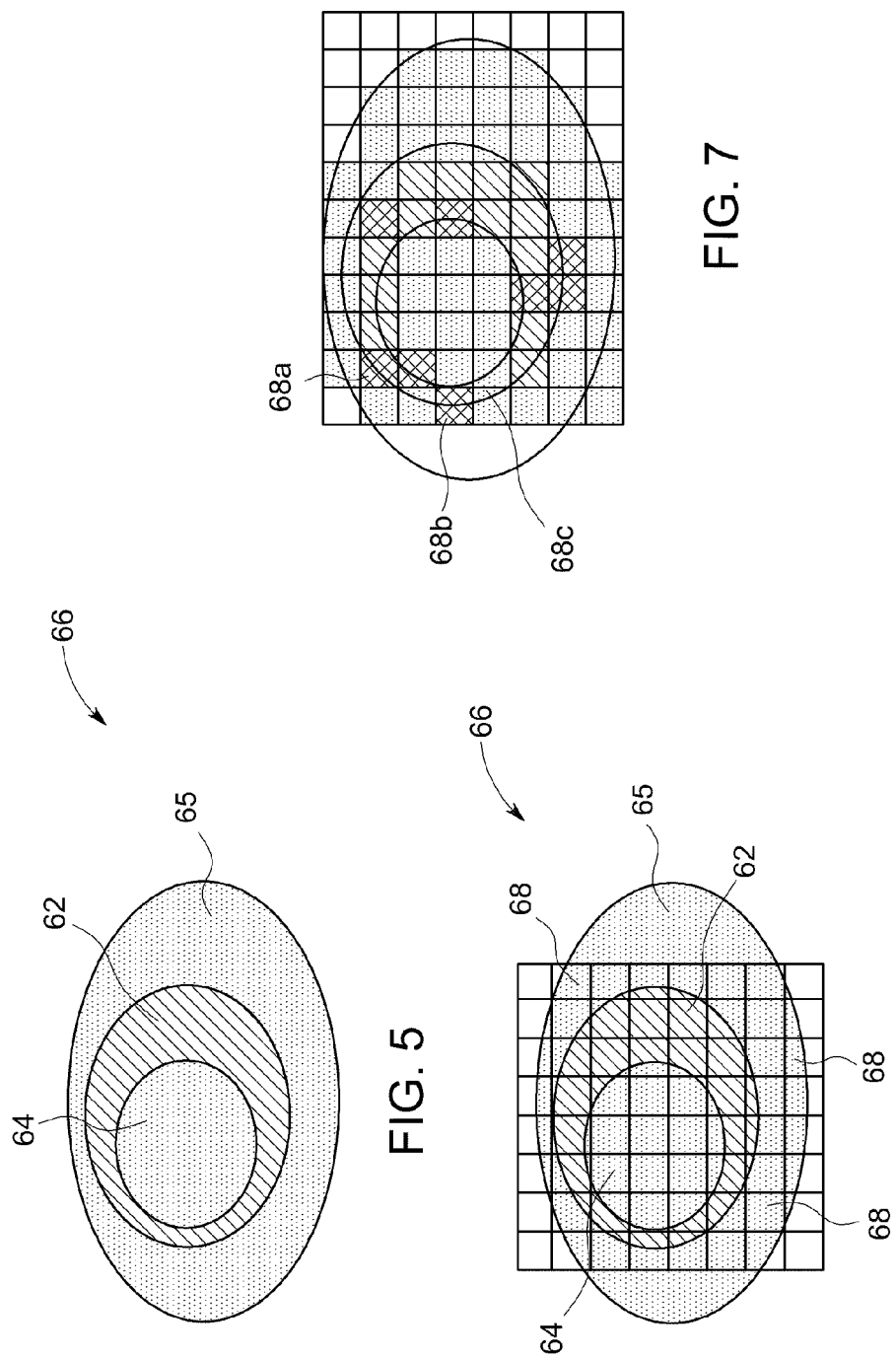

SYSTEMS AND METHODS FOR IDENTIFYING BONE MARROW IN MEDICAL IMAGES

BACKGROUND OF THE INVENTION

The subject matter disclosed herein relates generally to systems and methods for identifying bone marrow in images, and more particularly to detecting and segmenting images generated using computed tomography (CT) imaging systems to identify bone marrow.

Bone marrow is a radiosensitive tissue that is susceptible to damage from radiation exposure, such as from x-ray scans, CT scans, radioisotope administration, radiation therapy, etc. Thus, identification of bone marrow is important in order to evaluate and/or minimize radiation exposure to the bone marrow. For example, it is important to identify bone marrow during radiation therapies, such as radionuclide therapies to avoid myelotoxicity.

Methods to calculate radiation dose to bone marrow, for example the internal dosimetry schema of the Medical Internal Radiation Dose (MIRD), generally require knowledge of a patient's total skeletal active marrow mass. The value for this marrow mass cannot currently be directly measured. In order to measure the full mass of bone marrow, the inner part of each bone that is imaged must be identified. In current practice, this is performed manually by a user tracing the regions on the full body image slices of an imaged patient. This process is very tedious and time-consuming.

BRIEF DESCRIPTION OF THE INVENTION

In accordance with various embodiments, a method for identifying bone marrow in medical image data is provided. The method includes obtaining a three-dimensional (3D) computed tomography (CT) volume data set corresponding to an imaged volume and identifying voxels in the 3D CT volume data set having a Hounsfield Unit (HU) value below a bone threshold. The voxels are identified without using image continuity. The method further includes marking the identified voxels as non-bone voxels, determining definite tissue voxels based on the identified non-bone voxels and expanding a region defined by the definite tissue voxels. The method also includes segmenting the expanded region to identify bone voxels and bone marrow voxels and identifying bone marrow as voxels that are not the bone voxels.

In accordance with other embodiments, a method for identifying bone marrow in medical images is provided. The method includes identifying bone regions in a three-dimensional (3D) image based on a bone threshold value and segmenting non-bone regions from the 3D image having the identified bone regions, wherein boundaries for the segmenting are determined from the identified bone regions. The method further includes identifying bone marrow regions in the 3D image as regions not identified as bone regions or segmented as non-bone regions.

In accordance with yet other embodiments, a computed tomography (CT) imaging system is provided that includes a gantry supporting an x-ray source and a detector array for rotatable operation to scan a patient to acquire a three-dimensional (3D) image data set. The CT imaging system further includes an image reconstructor configured to reconstruct a 3D image of the patient using the 3D image data set and a bone marrow segmentation module configured to automatically segment bone marrow in the reconstructed 3D image.

BRIEF DESCRIPTION OF THE DRAWINGS

FIG. 5 is a diagram illustrating a cross-section of a bone.

FIG. 6 is a diagram illustrating image pixels corresponding to a region of the cross-section of the bone of FIG. 5.

FIG. 7 is a diagram illustrating pixels that may cause artifact bridges to occur in an imaged bone.

DETAILED DESCRIPTION OF THE INVENTION

Figure 1:
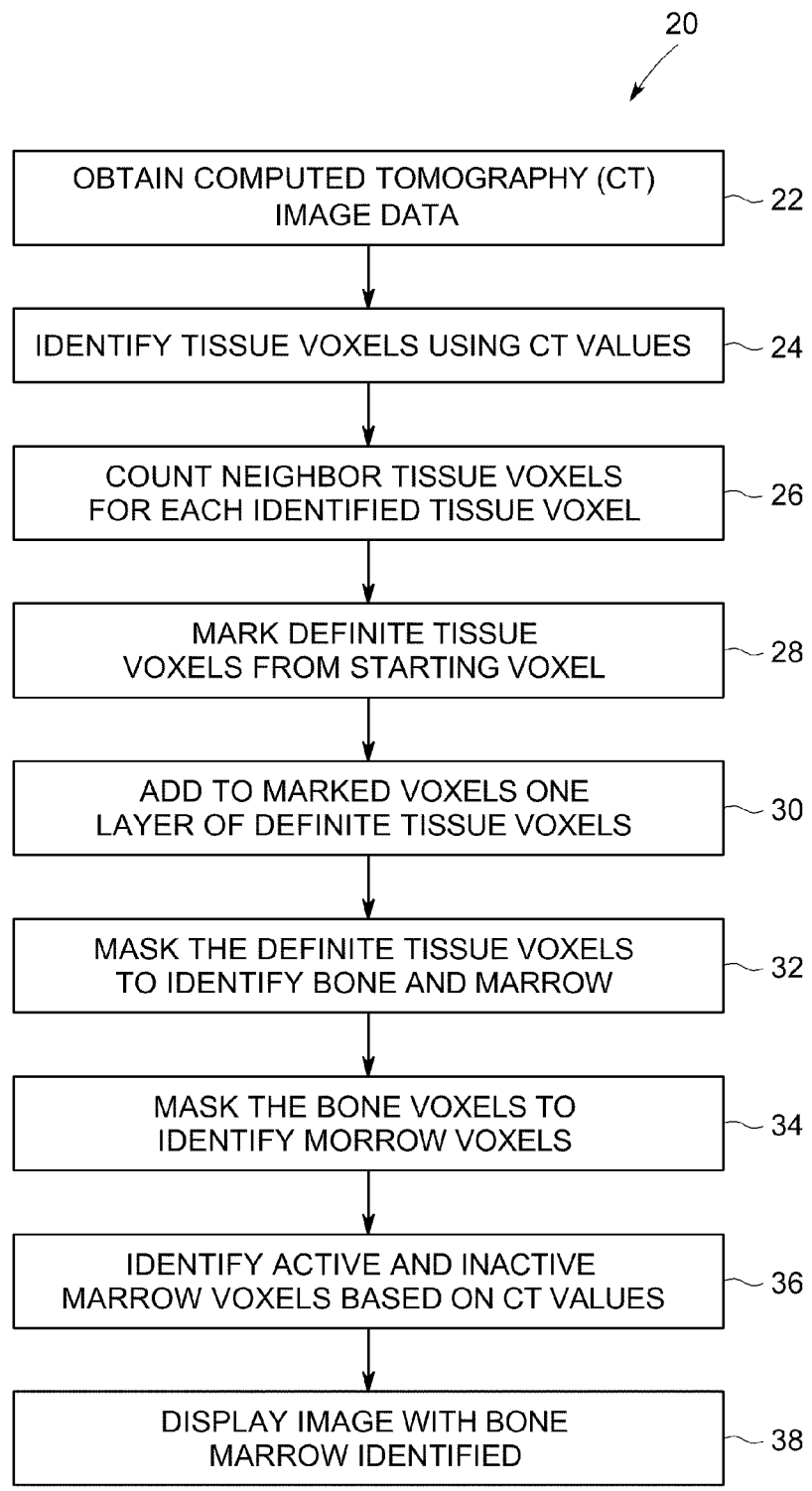
FIG. 1 is a flowchart of a method for identifying bone barrow in a computed tomography (CT) image data set in accordance with various embodiments.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "reconstructing an image" is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Various embodiments provide systems and methods for bone marrow segmentation and/or detection to identify bone marrow in computed-tomography (CT) images. Using thresholding and segmentation based on Hounsfield units, bone marrow is identified by detecting all bone cavities and thereafter the bone marrow may be divided based on active (e.g., blood) and inactive (e.g., fat) portions or bands. At least one technical effect of the various embodiments is a faster, more reproducible method for automatically segmenting bone marrow from images, particularly CT images.

Figure 2:
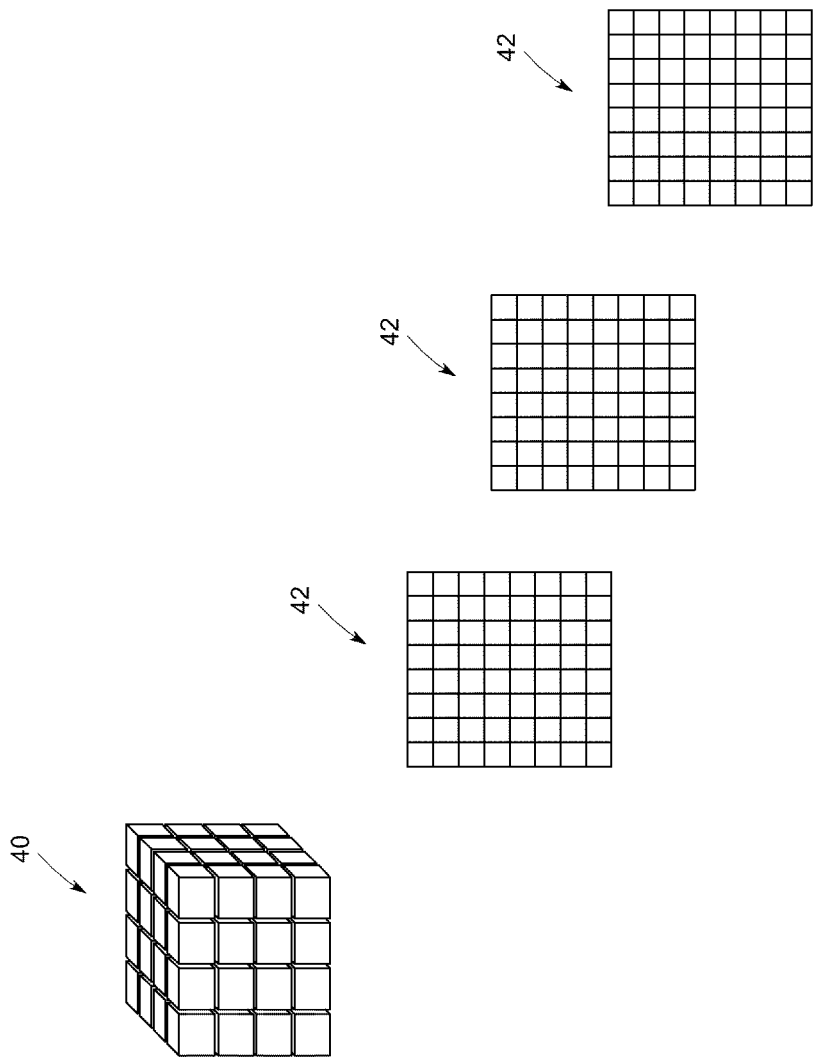
FIG. 2 illustrates a three-dimensional (3D) image volume formed from a stack of two-dimensional (2D) image slices from which bone marrow may be segmented in accordance with various embodiments.

Specifically, various embodiments provide a method 20 as illustrated in FIG. 1 for identifying bone barrow in a CT image data set, particularly a three-dimensional (3D) image volume 40 (as shown in FIG. 2) having a plurality of image voxels corresponding to image data acquired by a CT imaging system. The method 20 may be performed automatically to segment and identify bone marrow voxels in the 3D image volume. It should be noted that the 3D image volume 40 is generally formed from a plurality of two-dimensional (2D) image slices 42 arranged in a stack.

Figure 3:
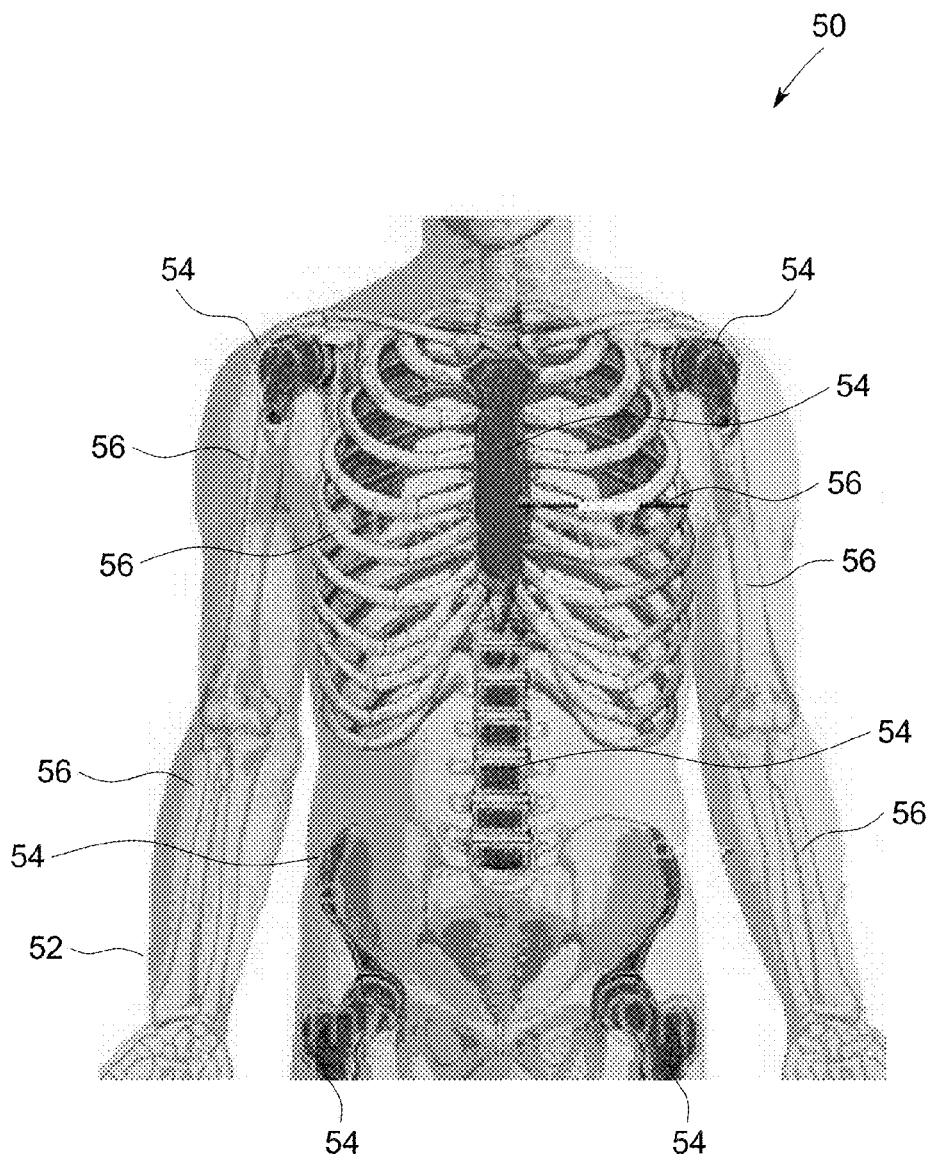
FIG. 3 is an illustration representing a human torso showing bone marrow that is automatically segmented and identified in accordance with various embodiments.

As shown in FIG. 3, the 3D volume may be all of or a portion of an imaged individual. For example, a representation 50 of a human torso 52 is illustrated showing bone marrow 54 in bones 56 of the human torso 52 that are automatically segmented and identified by the method 20. Thus, the method 20 segments the bone marrow 54 from bone 56.

In particular, and referring to the method 20 of FIG. 1, at 22 CT image data is obtained, for example, from a CT scan of a patient or a portion of a patient. Although the method 20 is described in connection with a whole body CT scan, the method 20 may be implemented in connection with 3D image volume data for less than the entire patient, namely less than the whole body CT scan. The 3D image volume data may be acquired by any x-ray imaging system, such as any diagnostic or clinical CT imaging system. For example, in an axial scan of a patient (or a portion of the patient), an x-ray source and a detector array are rotated with a gantry within an imaging plane and around the patient to be imaged such that the angle at which the x-ray beam intersects the patient constantly changes. A group of x-ray attenuation measurements, known as projection data, from the detector array at one gantry angle is referred to as a view. A scan of the patient comprises a set of views made at different gantry angles, or view angles, during one revolution of the x-ray source and detector.

The projection data is processed to construct an image that corresponds to a 2D slice taken through the patient. One method for reconstructing an image from a set of projection data is referred to in the art as the filtered back projection technique. This process converts the attenuation measurements from a scan into integers called CT numbers or Hounsfield Units (HU), which are used to control the brightness of a corresponding pixel on a cathode ray tube display.

Figure 4:
FIG. 4 is a CT image corresponding to a 3D CT image data set from which bone marrow may be segmented in accordance with various embodiments.

Accordingly, in various embodiments, the 3D image volume data includes image data having an HU value for each of the voxels in the imaged 3D volume. Thus, for example, as shown in the image 60 of FIG. 4, image data may be obtained corresponding to an imaged patient, wherein each of the image voxels has a corresponding HU value. Although the image 60 generally shows only a portion of the patient, the 3D image volume data in various embodiments corresponds to an entire body scan of the patient.

Because of inaccuracies and partial volumes, the tissue and marrow may appear to be joined or connected in the 3D image volume. For example, in lower resolution CT imaging systems, artifact bridges may be present between tissue and marrow, resulting in the marrow appearing to be tissue, namely not enclosed in bone. These artifact bridges are greater near bone joints and other locations where bone is thin. For example, as illustrated in FIG. 5, showing a cross-section of a bone 62 with marrow 64 therein, such as an arm, the bone 62 is surrounded by tissue 65 with air 66 outside the tissue. As illustrated in FIG. 6, a plurality of image pixels 68 (e.g., corresponding to a pixelated detector) acquire image information of the 3D image volume. It should be noted that the pixels 68 correspond to image slices that are used to form the 3D image volume. As can be seen, depending on the size of the pixels 68, and particularly for larger sized pixels, which are used to generate better image quality, artifact bridges may result as shown in FIG. 7. It should be noted that the number of pixels 68 in the x and y directions may the same or different.

As illustrated in FIG. 7, because of the larger size of the pixels, resulting in limited resolution, partial volume effects and inaccuracies can result as illustrated by the pixel 68a. Moreover, as illustrated by the pixel 68b, a CT value may be between that of bone and tissue and may be incorrectly identified as tissue. As can further be seen at pixel 68*c*, marrow and tissue may appear to be connected.

Figure 8:
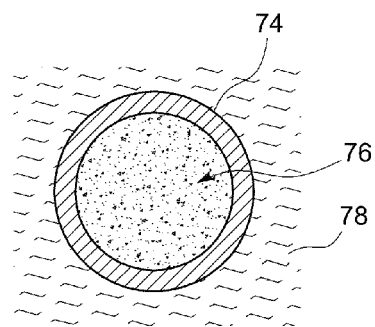
FIG. 8 is a diagram illustrating an image slice of a normal bone.
Figure 9:
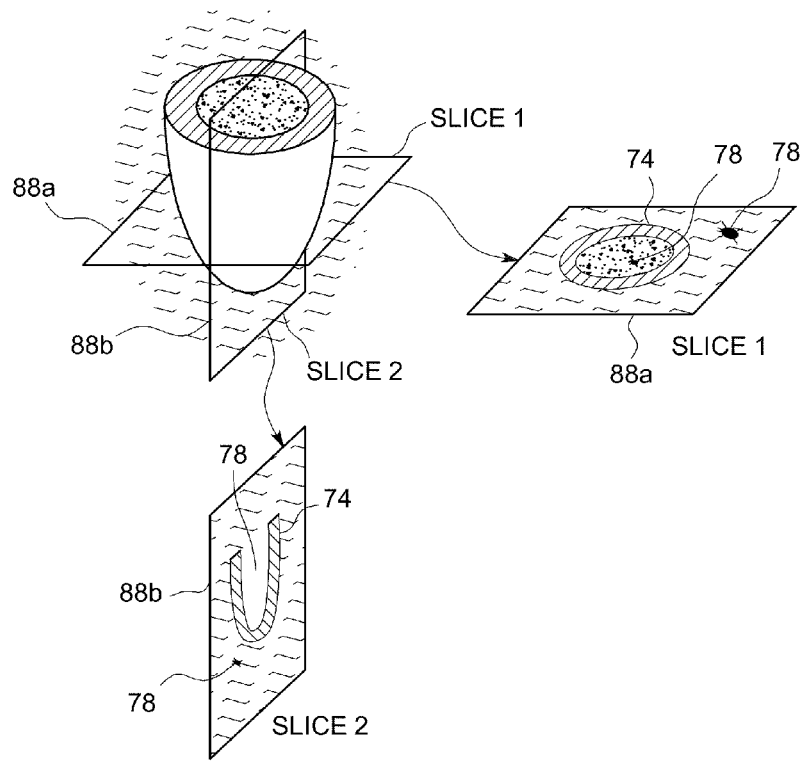
FIG. 9 is a diagram illustrating different image slices of a cup-like bone without marrow.

Moreover, it also should be noted that tissue may also appear like marrow when viewing individual image slices. For example, in a slice of a normal bone as illustrated in FIG. 8, illustrating a large bone (e.g., leg bone), marrow 76 in the image slice appears completely enclosed by bone 74 and separated from tissue 78. However, in other bones, for example, cup-like bones without marrow (e.g., some vertebrae having concave indentions or a portion of the pelvis) and having tissue inside and outside the bone, depending on the orientation of the image slice 88, for example, a transverse image slice 88*a* versus a saggital image slice 88*b*, the bone 74 in the transverse image slice 88*a* may appear to enclose tissue, namely bone marrow. However, in the saggital image slice 88*b*, it is clear that the tissue is not bone marrow.

Accordingly, the method 20 segments marrow from bone using 3D image volume data such that bone marrow tissue is distinguished from non-bone marrow tissue. In particular, and referring again to the method 20 of FIG. 1, after obtaining the 3D image volume data, voxels corresponding to imaged tissue are identified. In particular, at 24 image voxels below a bone HU threshold value, which defines a bone threshold, are identified and marked. For example, image voxels having a value below 200 HU are identified and marked in the volume data set, which corresponds to non-bone voxels. It should be noted that although the various steps of the method 20 may be described and illustrated in connection with pixels in a 2D slice, the method 20 is performed in connection with a 3D image volume.

Figure 10:
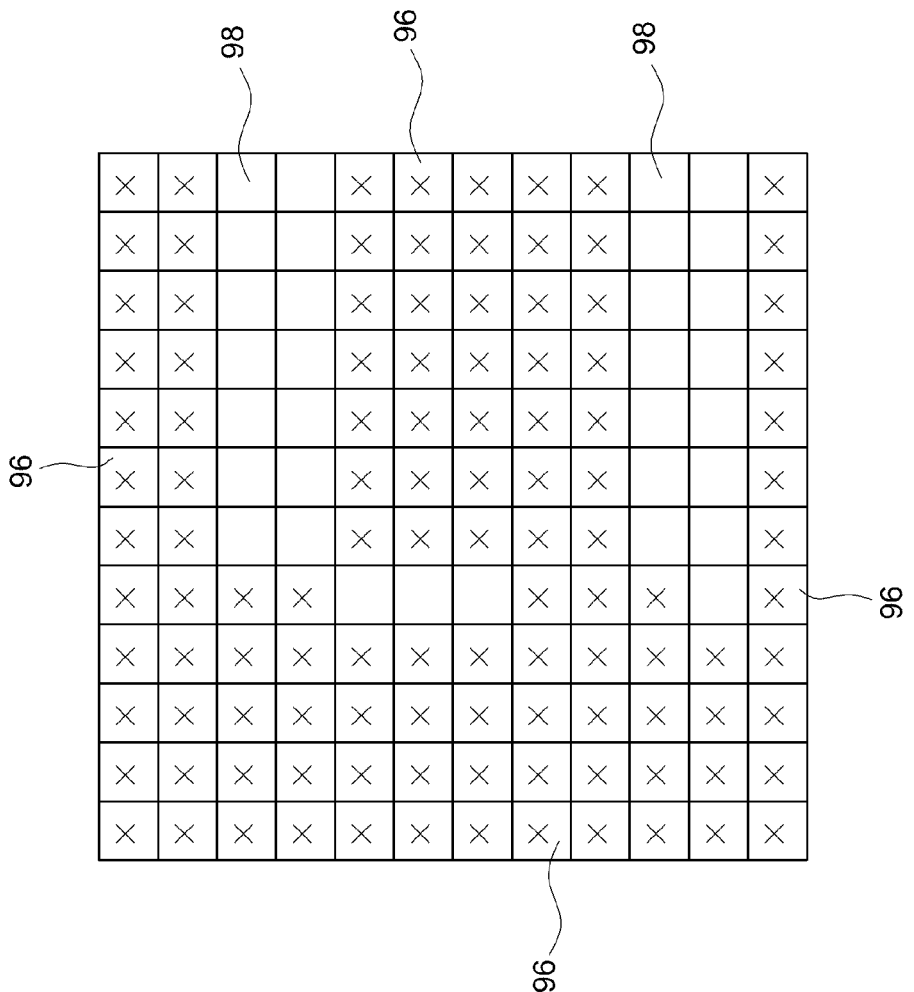
FIG. 10 is a diagram illustrating marking of tissue pixels in accordance with various embodiments.

This identification and marking process at 24 is illustrated in FIG. 10 wherein tissue pixels 96, for example, air, tissue and marrow pixels are marked and non-tissue pixels 98 are not marked based on the HU value for each pixel. Thus, the bone HU threshold value is selected such that all voxels below the HU value are either air, tissue or marrow voxels. The tissue identification process at 24 is performed on the entire data set without using or imposing any image continuity. Accordingly, no continuity is required between adjacent voxels, for example, such that the voxels have to be in the same bone, etc. Thus, every voxel in the 3D data set having an HU value below 200 is identified and marked as a voxel corresponding to tissue. It should be noted that different HU threshold values may be used as desired or needed, for example, 250 HU, 300 HU, etc.

Figure 11:
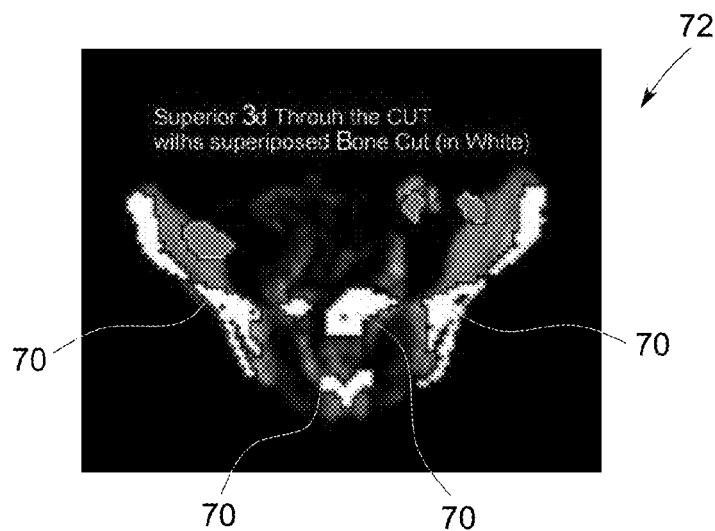
FIG. 11 is an image slice showing imaged bone to be segmented in accordance with various embodiments.
Figure 12:
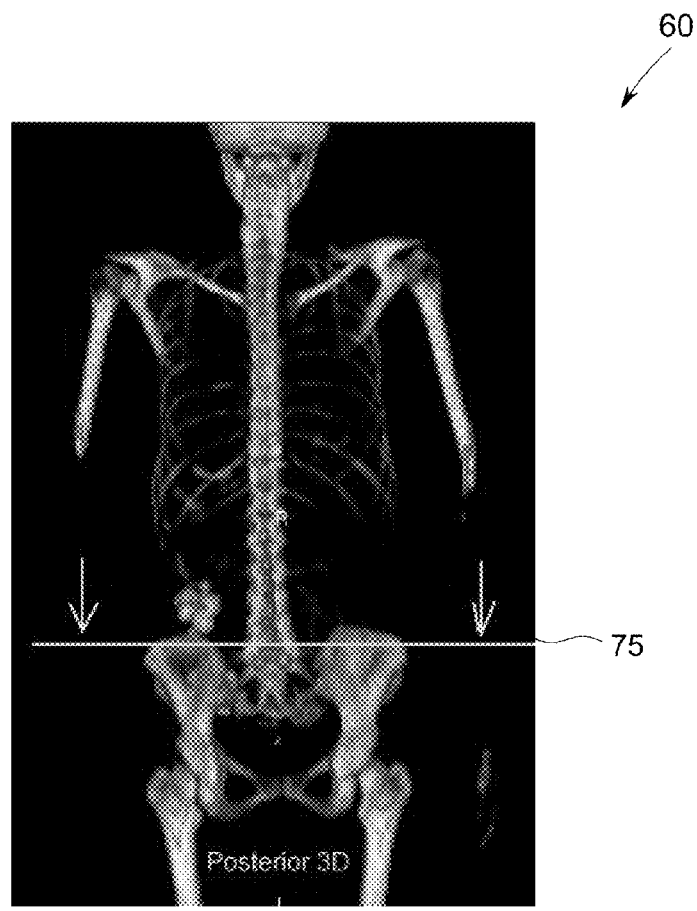
FIG. 12 is a CT image corresponding to 3D CT image data from which the image slice of FIG. 11 was generated.

Accordingly, the marked voxels correspond to any imaged non-bone portions in the body. In general, the marking identifies all tissue, including bone marrow, and air, in the imaged 3D volume, namely all voxels that are not bone. For illustrative purposes, voxels 70 as shown in the image slice 72 of FIG. 11 corresponding to slice through the image volume as indicated by the line 75 in FIG. 12 are not marked because the voxels have an HU value above 200, which corresponds to hard bone. It should be noted that although an image slice is shown, the identification and marking of tissue voxels is performed on the 3D data set as a whole. Accordingly, each voxel having a non-bone HU value, namely a tissue HU value that has been identified, is marked, for example, flagged in the 3D volume data set.

Figure 13:
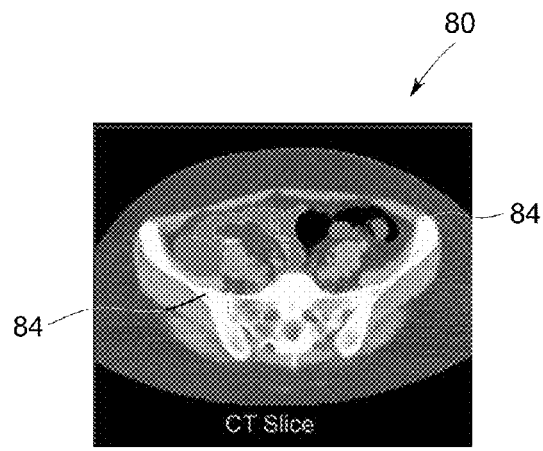
FIG. 13 is a CT image slice illustrating a portion of a 3D CT image data set.
Figure 14:
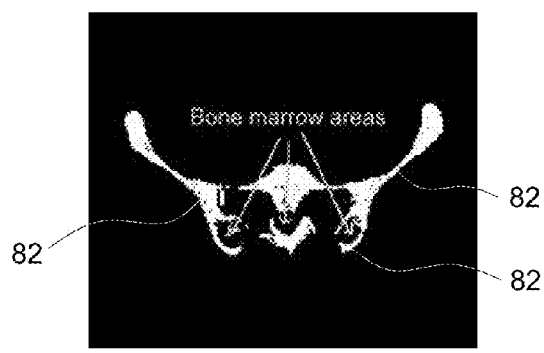
FIG. 14 is an image showing bone regions segmented by the various embodiments.
Figure 15:
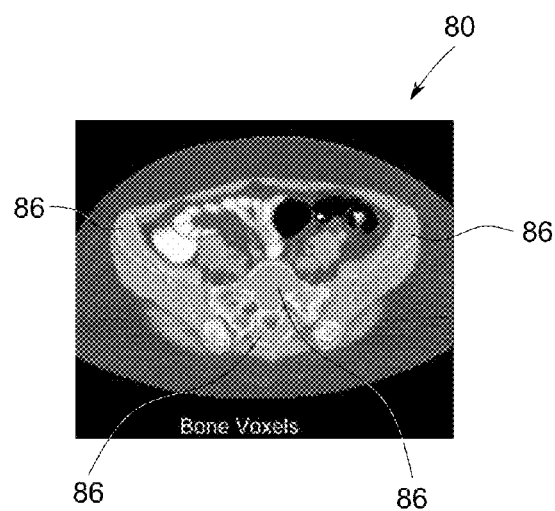
FIG. 15 is a CT image slice illustrating bone voxels segmented in accordance with various embodiments.

Thus, for example, as shown in the CT image slice 80 of FIG. 13, bones 84, such as hard bones, in the 3D volume are not identified with the remaining non-bone regions marked using the bone threshold. Accordingly, as shown in FIG. 14, bone tissue areas surrounding the bones 84 and marrow areas surrounded by the bones 84 (shown in FIG. 13) are marked. Thus, as shown in FIG. 15, all voxels that are not bone voxels (bone voxels are represented by the shaded regions 86), are identified and marked based on the bone threshold.

Figure 16:
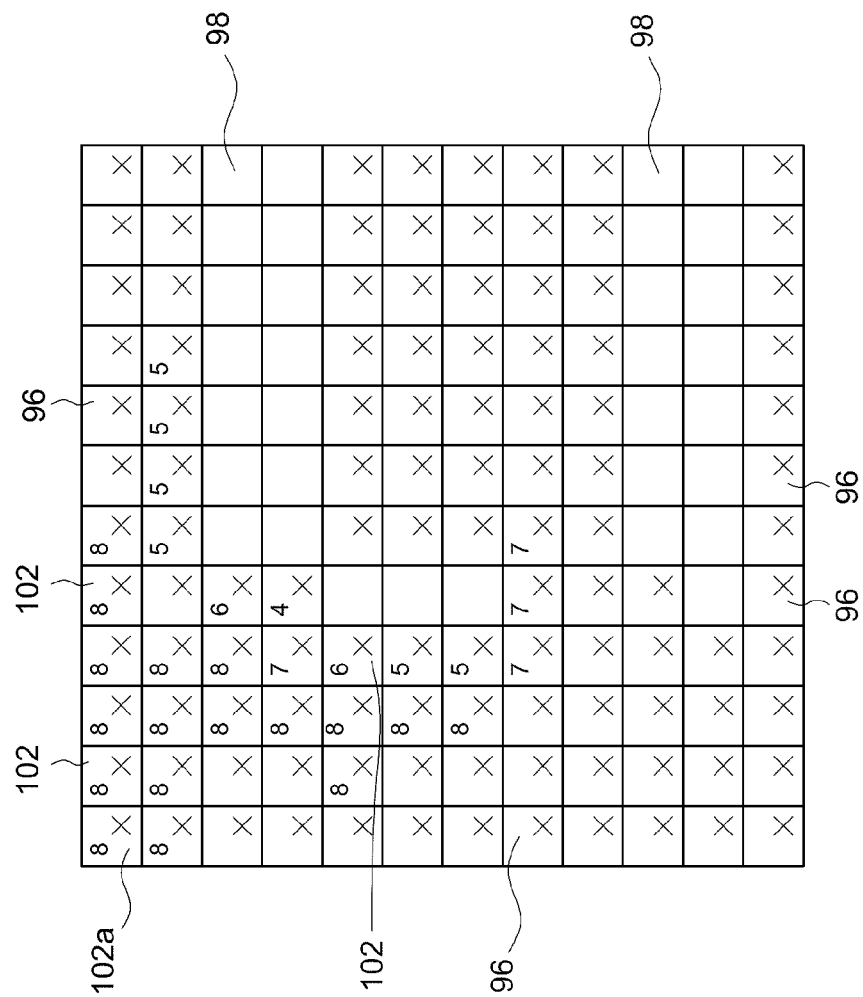
FIG. 16 is a diagram illustrating a neighbor tissue pixel counting process in accordance with various embodiments.

Thereafter, and referring again to the Method 20 of FIG. 1, at 26, for each of the identified tissue voxels, each neighbor or adjacent voxel that is also a tissue voxel is counted and the count recorded for that tissue voxel. For example, as shown in FIG. 16, which again illustrates pixels for simplicity, a number 102 corresponding to neighbor pixels (to one of the pixels) that are also tissue pixels 96, which may include adjacent pixels in the x and y directions, as well as diagonally, is recorded in connection with each tissue pixel 96. In various embodiments, a voxel length of one is used such that a 3×3×3 box of neighbor voxels are evaluated to determine if any of the twenty-six neighbor voxels are tissue voxels. However, it should be noted that the determination may be increased to more voxels that are adjacent to the voxel of interest, such as two voxels away. It also should be noted that a fuzzy logic may be used wherein the number of neighbors is defined by a threshold.

Once tissue voxels have been identified and the respective count value determined for each, definite tissue voxels are marked at 28 (in the method 20 of FIG. 1) as described below, which is determined based on the recorded count values. The marking process at 28 begins at a starting voxel that is a non-bone voxel. For example, in a CT volume set of a full body scan, the initial voxel may be selected at the top left corner (illustrated as pixel 102*a* in FIG. 16) of the 3D data set, which will be an air voxel outside the patient body, namely air imaged within a bore of the CT scanner. However, any voxel may be selected as the initial voxel that is not a bone voxel.

Figure 17:
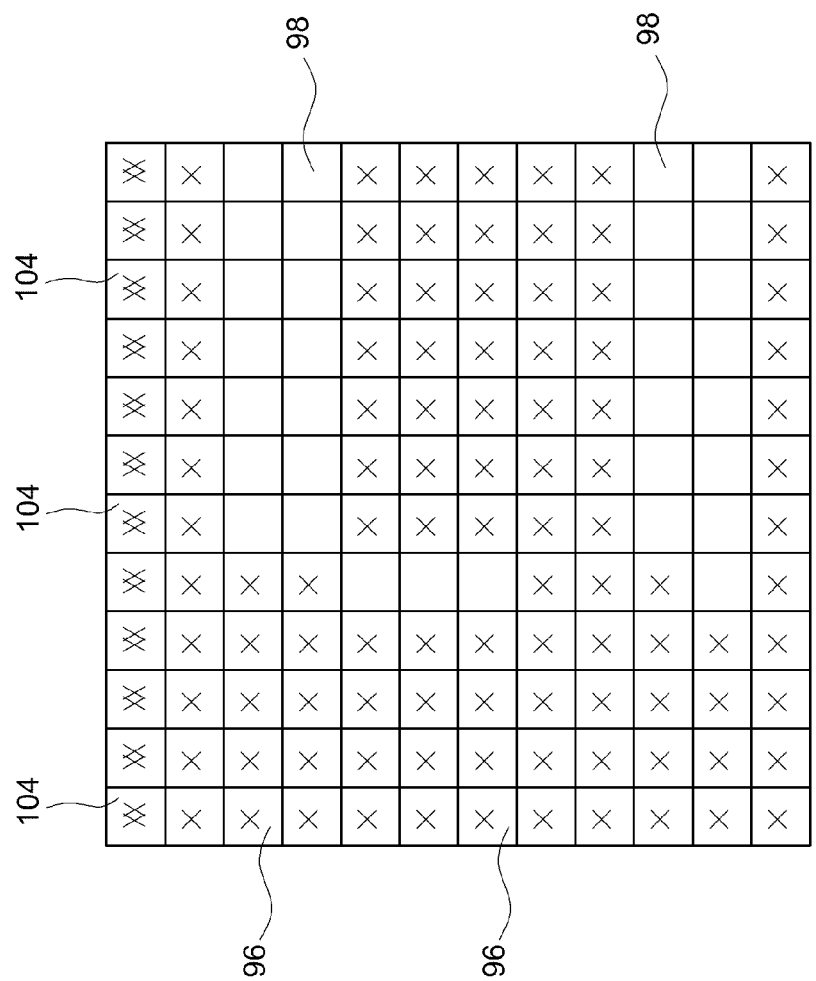
FIG. 17 is a diagram illustrating the start of a process of marking definite tissue pixels in accordance with various embodiments.
Figure 18:
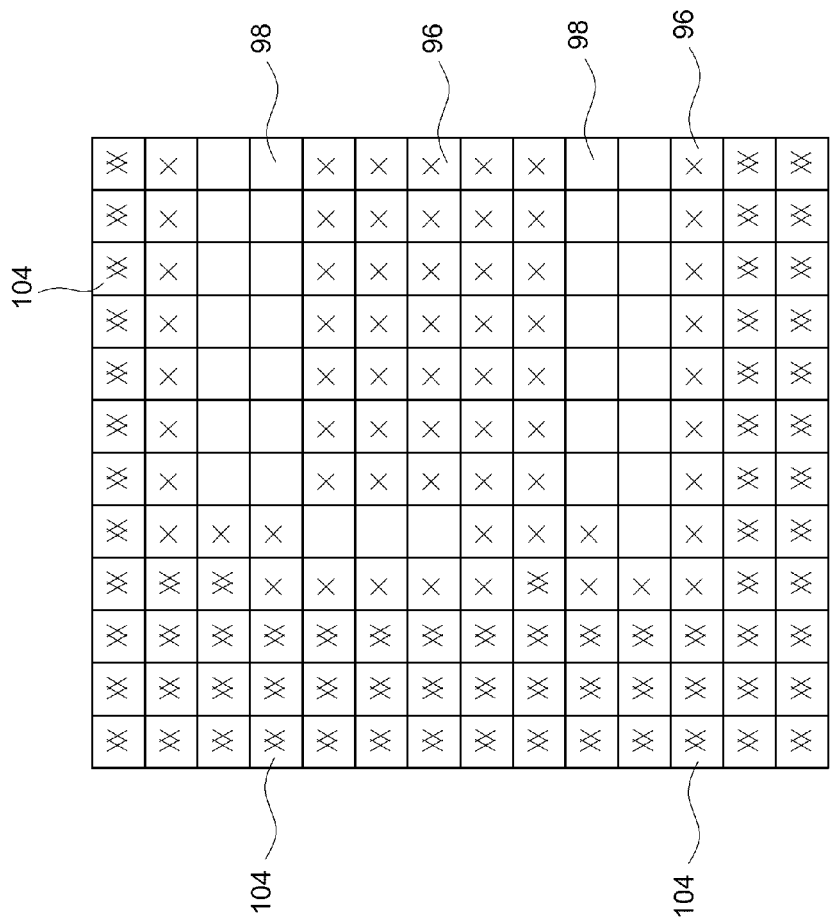
FIG. 18 is a diagram illustrating the completion of marking definite tissue pixels in accordance with various embodiments.

The definite tissue voxels are then marked as illustrated in FIG. 17, which illustrates the start of the process of marking definite tissue pixels 104, which again is illustrated for one slice of the image volume for simplicity. In various embodiments, the definite tissue pixels 104, namely pixels that are not bone pixels (e.g., definitely not bone pixels), are identified starting from the corner pixel in the illustrated example, as pixels that are surrounded by only tissue pixels 96 (as determined from the count value) and that are connected to the corner pixel 102*a* (shown in FIG. 16) by other pixels that have been identified as definite tissue pixels 104. It should be noted that in FIG. 17, only the start of the process of marking of definite tissue pixels 104 is illustrated. Accordingly, all of the definite tissue pixels 104 are not necessarily shown as marked in FIG. 17, but are all shown as marked in FIG. 18.

Figure 19:
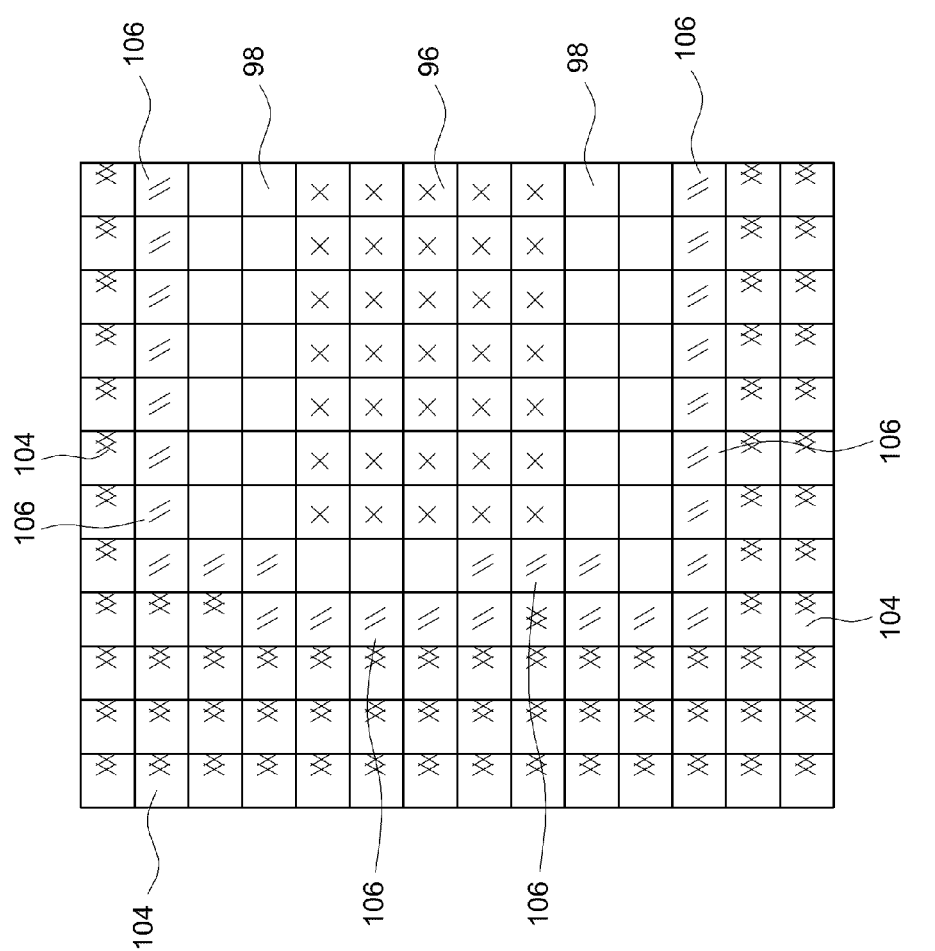
FIG. 19 is a diagram illustrating a region growing process in accordance with various embodiments.

Thereafter, a region growing process is performed. In various embodiments, the region growing process includes adding voxels to the identified definite tissue voxels, for example, one or more layers of voxels. For example, at 30 (in the method 20 of FIG. 1) and as illustrated in FIG. 19 (again illustrated as pixels in an image slice for simplicity), a layer of pixels 106 is added to dilate the region defined by the definite tissue pixels 104. For example, a layer of pixels 106 may be added generally inwards or towards the tissue pixels 96 that were not marked as definite tissue pixels 104. It should be noted that more than one layer of voxels (illustrated as pixels) may be added.

Figure 20:
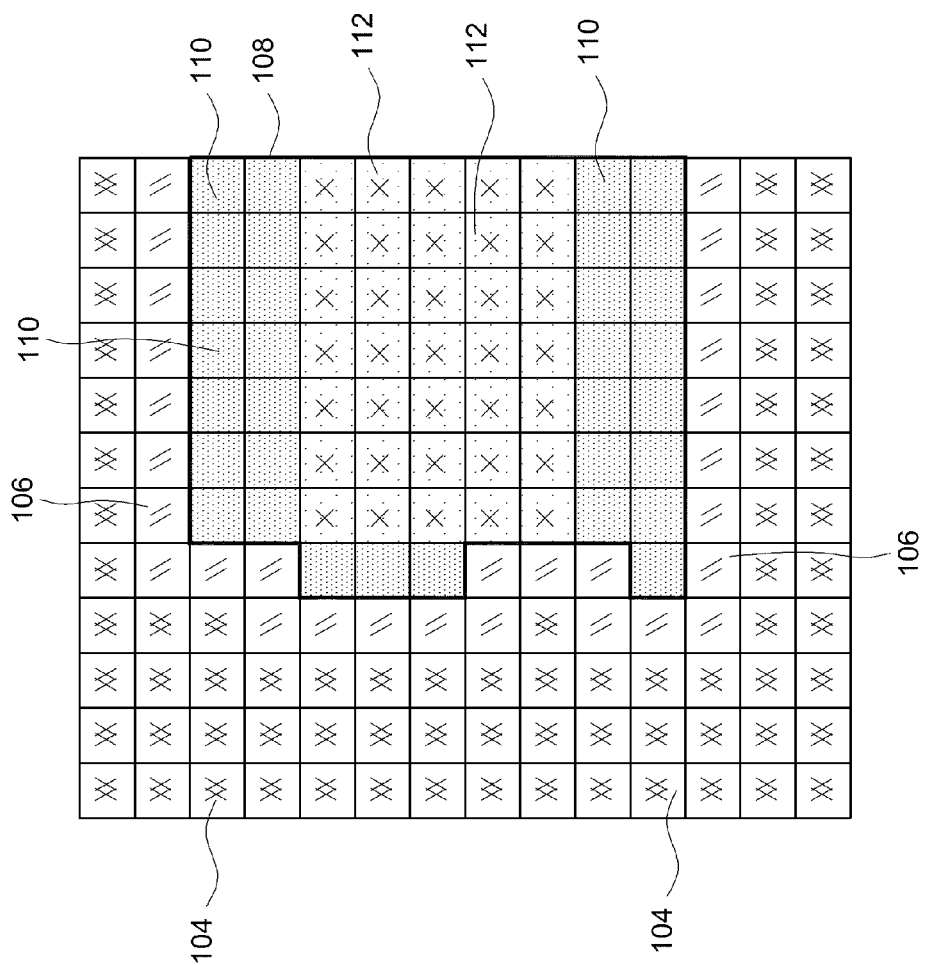
FIG. 20 is a diagram illustrating the identification of bone and marrow in accordance with various embodiments.
Figure 21:
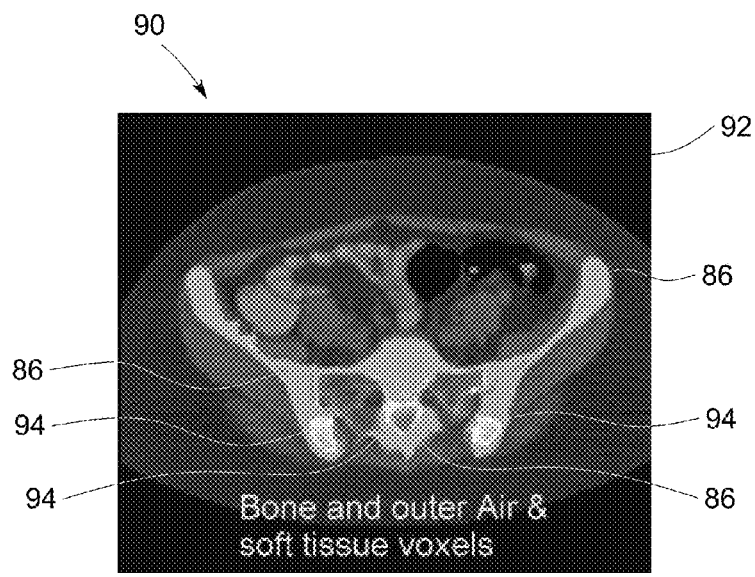
FIG. 21 is a CT image slice illustrating non-bone regions surrounding bones marked in accordance with various embodiments.

Thereafter, the definite tissue voxels are masked at 32 (in the method 20 of FIG. 1) to identify bone and marrow. For example, as shown in FIG. 20, again illustrating an image slice for simplicity, the definite tissue pixels 104 and the added layer of pixels 106 are masked such that a region 108 remains that includes pixels corresponding to bone and marrow only, which are illustrated as bone pixels 110, namely hard bone pixels, and marrow pixels 112. Accordingly, as shown in CT image slice 90 of FIG. 21, the bone voxels represented by the shaded regions 86 and the marrow regions 94 are identified by masking the definite tissue voxels (namely the soft tissue voxels), represented by the shaded region 92, which is the region outside of the bone voxels. Thus, all regions that are not tissue are identified.

Referring again to the method 20 of FIG. 1, thereafter, the bone voxels are masked at 34 to identify the marrow voxels, which are the voxels that area encased within bone and that do not have connectivity. For example, the non-tissue pixels 98 (shown in FIGS. 18 and 19), which are now identified as bone pixels 110 are masked to identify the marrow pixels 112. Accordingly, as shown in the CT image volume 100 of FIG. 22, the regions 94 now marked are the bone marrow regions. For example, the voxels corresponding to identified bone marrow may be highlighted, such as colored differently (e.g., colored red) than the grayscale voxels corresponding to non-marrow voxels.

Figure 22:
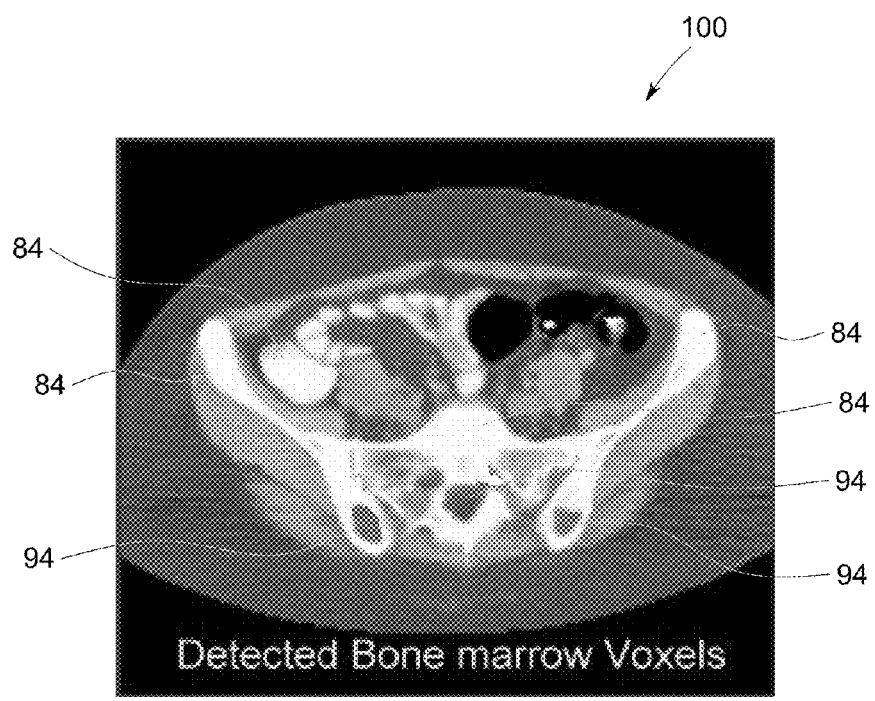
FIG. 22 is a CT image slice illustrating bone marrow regions marked in accordance with various embodiments.
Figure 23:
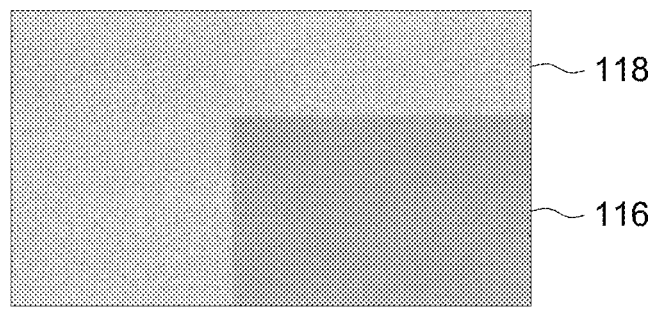
FIG. 23 is a diagram illustrating the identification of active and inactive bone marrow in accordance with various embodiments.

Thus, as shown in FIG. 22, only marrow voxels remain, from which active and inactive marrow may be identified based on CT values (HU values). For example, the different types of bone marrow may be identified, such as using a corresponding HU value for the marked bone marrow voxels. For example, red bone (active) marrow 116 and yellow (inactive) bone marrow 118 may be separately identified and marked as illustrated in FIG. 23. In general, red bone marrow consists mainly of myeloid tissue and yellow bone marrow consists mainly of fat cells. In some embodiments, marked voxels corresponding to a red marrow HU value and a yellow marrow HU value are identified, which may be ranges of HU values. For example, voxels having an HU value of about −49 and within a range thereof, for example, within 10 HU, are identified as yellow marrow and may be colored yellow in a displayed image. Voxels having an HU value of about 11 and within a range thereof, for example, within 10 HU, are identified as red marrow and may be colored red in a displayed image.

The CT image volume 100 with the identified bone marrow may then be displayed at 38. It should be noted that the CT image volume 100 only illustrates the display of marked red marrow voxels.

In accordance with various embodiments, and using the segmented and identified bone marrow voxels, different types of information may be determined and provided. For example, in a 3D volume data set including image data for a full body CT scan, the total mass of the bone marrow may be determined by summing all the marked pixels, with each pixel corresponding to a known mass volume (or weight) of the patient.

Figure 24:
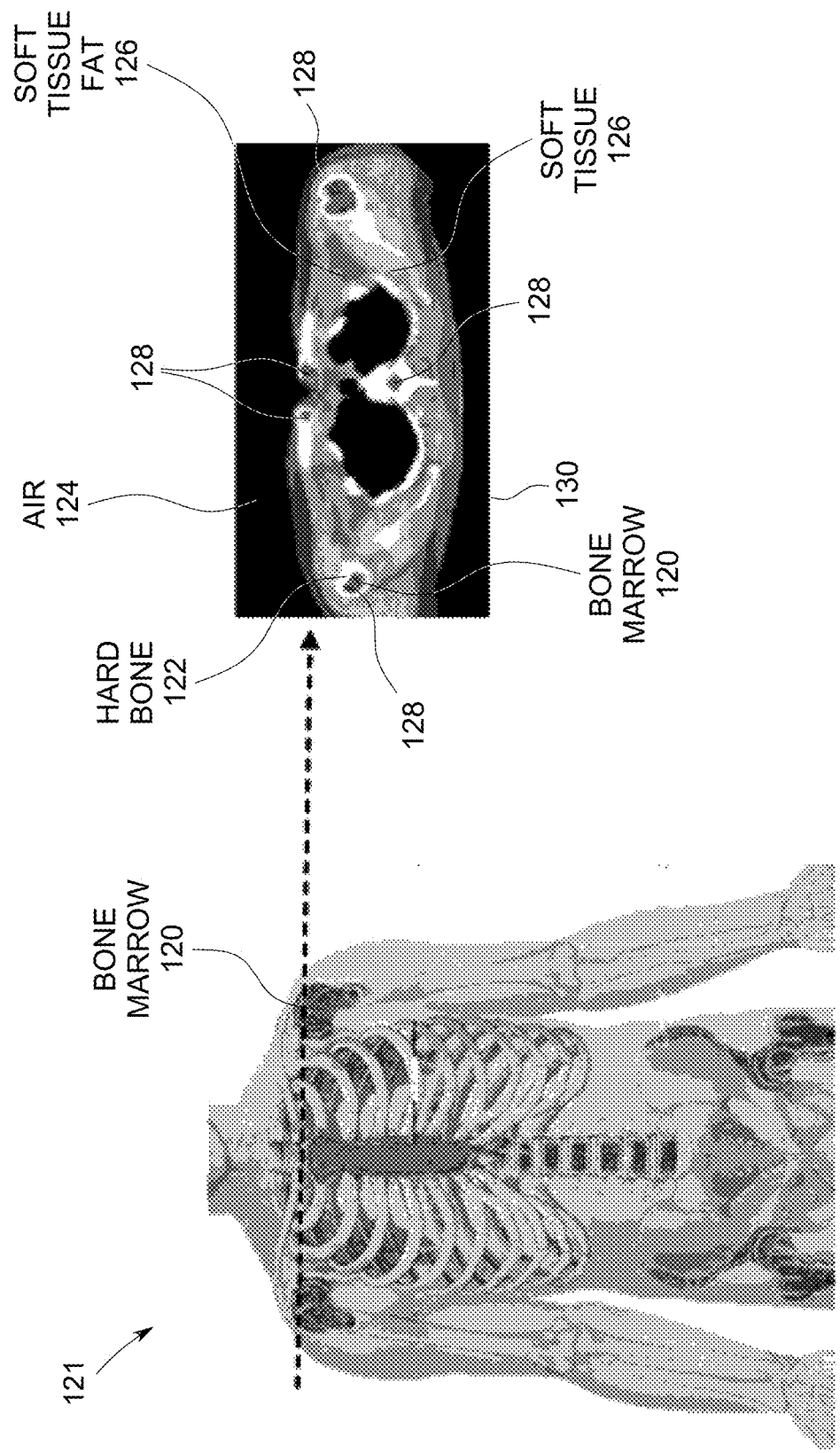
FIG. 24 is a diagram illustrating image segmentation in accordance with various embodiments to identify bone marrow.

Accordingly, as shown in FIG. 24, bone marrow 120 from a CT image of a patient 121 is automatically segmented in accordance with various embodiments. In particular, bone marrow 120 is segmented from hard bone 122, air 124 and soft tissue 126 and may be displayed as highlighted regions 128 in a displayed CT image slice 130.

It should be noted that if contrast agents are used during image acquisition, for example, Iodine in the blood or Barium for gastric track imaging, or if stents are present in the imaged region, these contrast agents and stents may cause artifacts and appear as bone due to large attenuation. Accordingly, in some embodiments, user intervention or user confirmation may be provided at one or more of the processing steps described herein.

Figure 25:
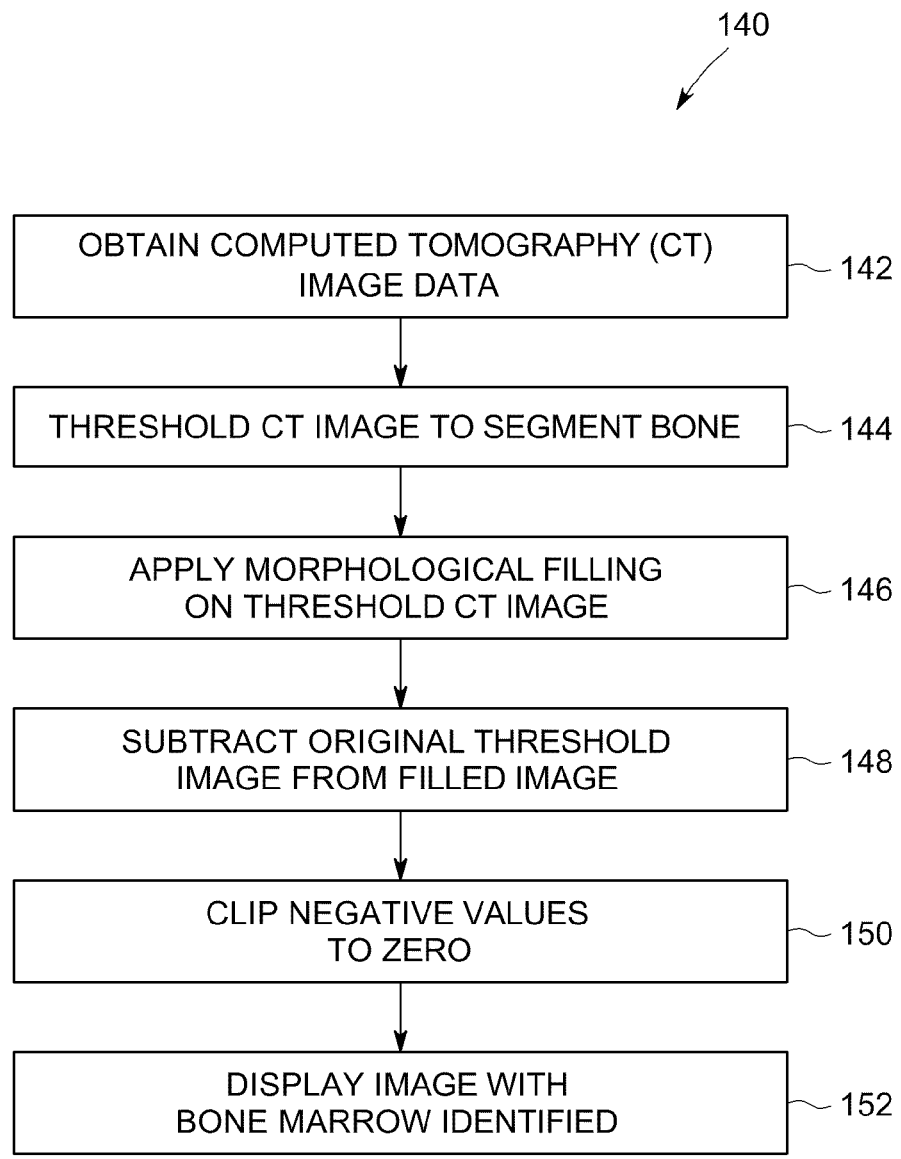
FIG. 25 is a flowchart of another method for identifying bone barrow in a CT image data set in accordance with various embodiments.

Variations and modifications to the various embodiments are contemplated. For example, various embodiments may provide a method 140 as shown in FIG. 25 to automatically segment bone marrow from CT images, such as for radiation dosimetry. As used herein, radiation dosimetry generally refers to the calculation of the absorbed dose in matter and tissue resulting from the exposure to indirect and direct ionizing radiation.

In particular, in accordance with various embodiments, the method 140 as shown in FIG. 25 may be provided for identifying bone barrow in a CT image data set, particularly a 3D image volume having a plurality of image voxels acquired by a CT imaging system. In particular, CT image data is acquired at 142, as described in more detail at 22 in FIG. 1.

Figure 26:
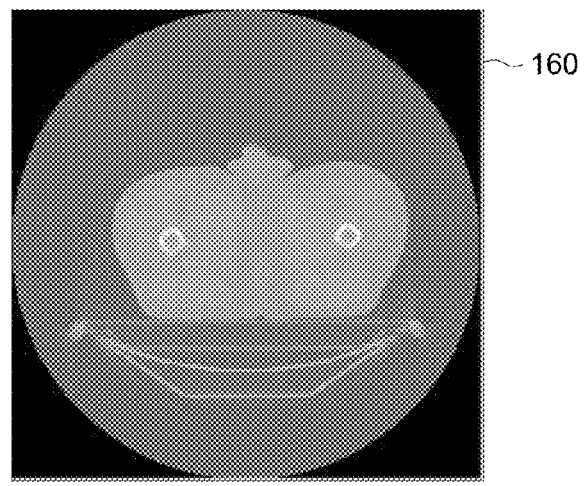
FIG. 26 is a CT image slice of a 3D CT volume from which bone marrow may be segmented in accordance with various embodiments.
Figure 27:
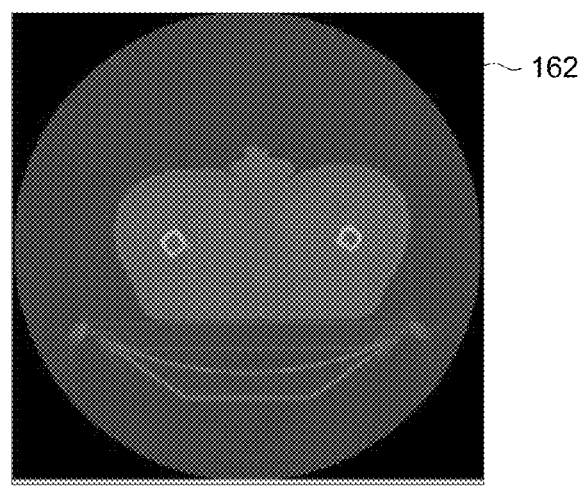
FIG. 27 is a CT threshold image corresponding to a thresholding process performed in accordance with various embodiments to identify bone.

Accordingly, a CT volume formed from CT image slices, for example, the CT image slice 160 shown in FIG. 26 may be obtained. Thereafter, at 144, thresholding is performed on the CT image to segment bone, for example, identify and mark bone voxels in the CT image. For example, a threshold image may be overlaid on the CT image 160 to form a CT threshold image 162 as shown in FIG. 27, which may include identifying voxels having an HU value greater than 200. Thus, the threshold image (thImg) is the CT image (ctImg) with image voxels having an HU value of greater than 200 identified such that thImg=ctImg>200.

Figure 28:
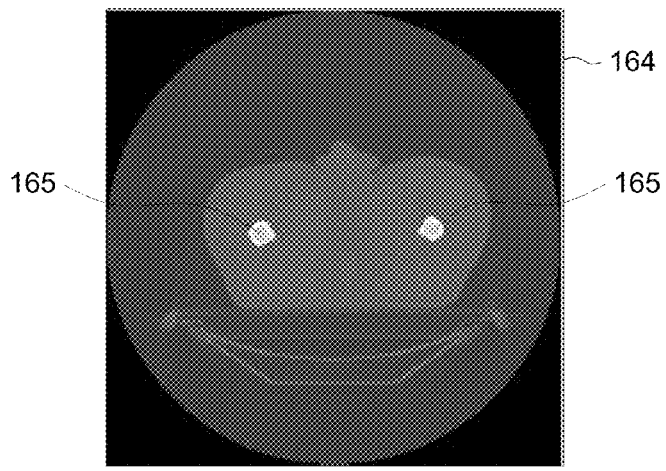
FIG. 28 is a CT image slice illustrating a morphologically filled image superimposed on a CT image formed in accordance with various embodiments.

Thereafter, a morphological filling, using any suitable 3D filling method is performed at 146 (in the method 140 of FIG. 25) on the threshold CT image. Morphological filling can be performed by 3D region growing from the bone boundaries in CT threshold image 162 wherein region growth is permitted through only those voxels that are completely encapsulated by the bone voxels. Thereafter, the CT image 160 is subtracted from the filled image at 148 (in the method 140 of FIG. 25), which may include overlaying the morphologically filled image (mFillImg) on the CT image 160 to form an image 164 as shown in FIG. 28 with regions 165 identified.

Figure 29:
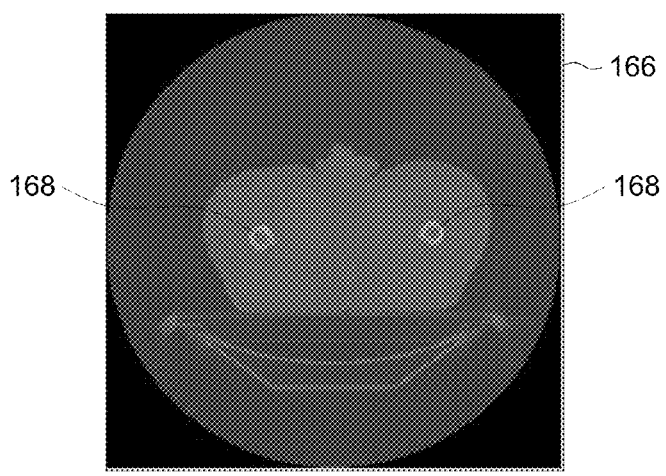
FIG. 29 is a bone marrow image formed in accordance with various embodiments.

Thereafter, at 150 (in the method 140 of FIG. 25), the negative HU values are clipped to zero, namely any voxels having a negative HU value are reset to a value of zero. The resulting image with bone marrow identified is then displayed at 152. For example, a bone marrow image may be overlaid on the CT image to form a bone marrow (boneMarrow) image 166 as shown in FIG. 29 with the bone marrow identified by the highlighted regions 168 (e.g., colored regions).

Figure 30:
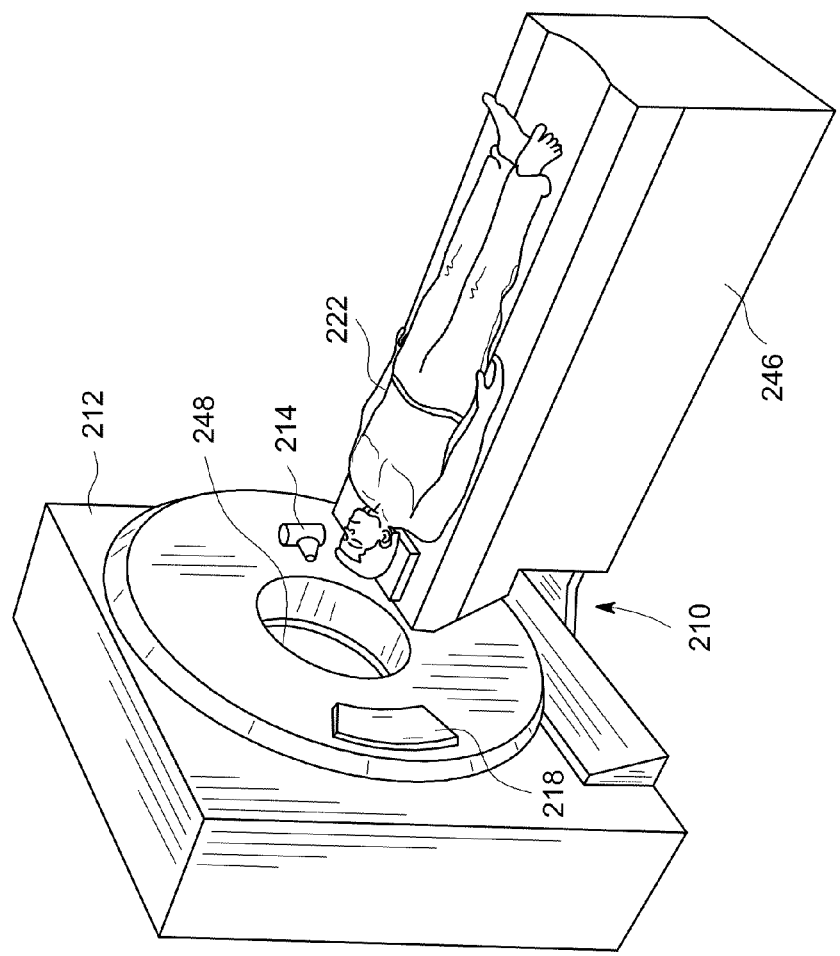
FIG. 30 is a pictorial drawing of a CT imaging system constructed in accordance with various embodiments.
Figure 31:
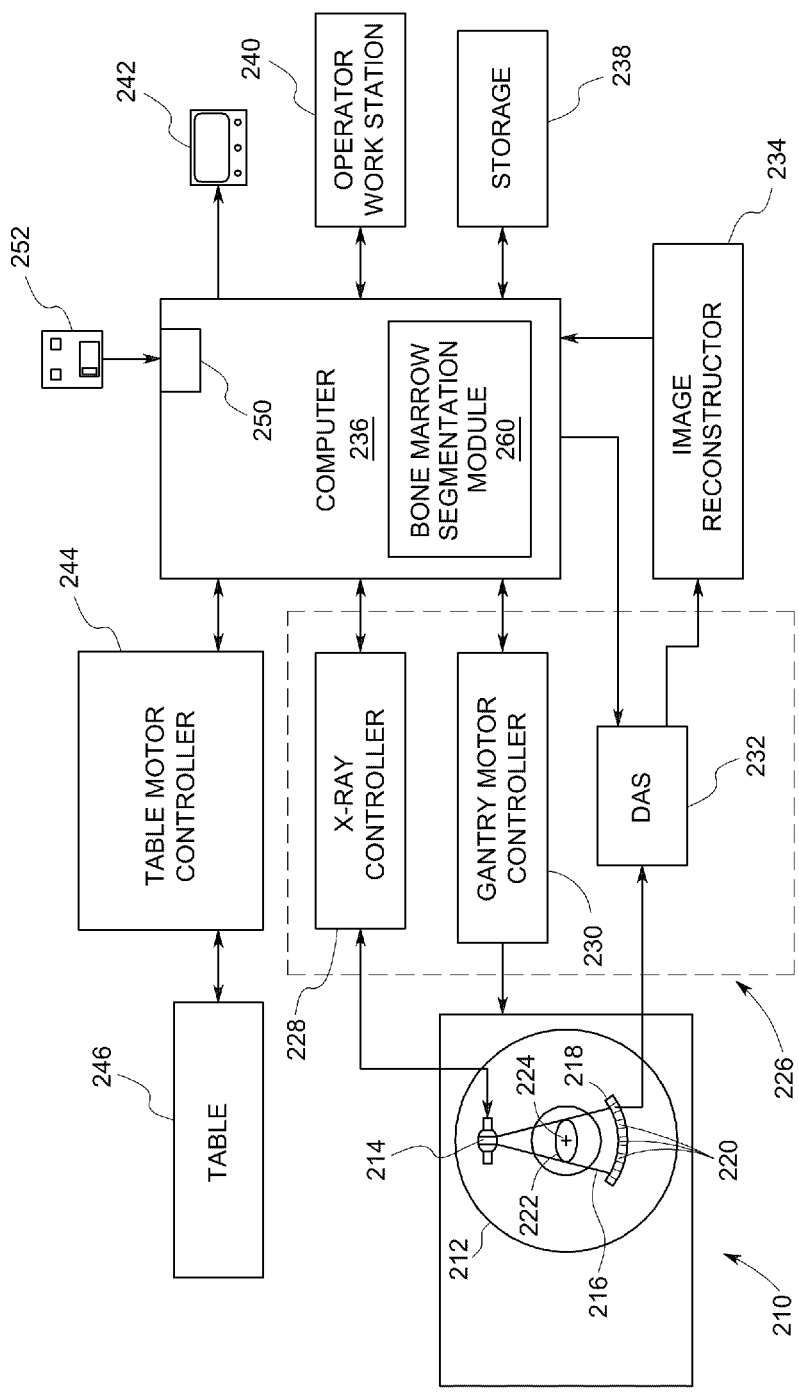
FIG. 31 is a schematic block diagram of the CT imaging system of FIG. 17.

Thus, various embodiments provide for automatically segmenting bone marrow from a CT image. The CT image data may be acquired by any suitable CT imaging system. For example, referring to FIGS. 30 and 31, a multi-slice scanning imaging system, for example, a CT imaging system 210 is shown as including a gantry 212. The gantry 212 includes an x-ray tube 214 (also referred to as an x-ray source 214 herein) that projects a beam of x-rays 216 toward a detector array 218 on the opposite side of the gantry 212. The detector array 218 is formed by a plurality of detector rows (not shown) including a plurality of detector elements 220 that together sense the projected x-rays that pass through an object, such as a medical patient 222 between the array 218 and the x-ray source 214. Each detector element 220 produces an electrical signal that represents the intensity of an impinging x-ray beam and hence can be used to estimate the attenuation of the beam (and determine HU values for image voxels as descried in more detail herein) as the beam passes through an object or the patient 222. During a scan to acquire x-ray projection data, the gantry 212 and the components mounted therein rotate about a center of rotation 224. FIG. 31 shows only a single row of detector elements 220 (i.e., a detector row). However, the multi-slice detector array 218 includes a plurality of parallel detector rows of detector elements 220 such that projection data corresponding to a plurality of quasi-parallel or parallel slices can be acquired simultaneously during a scan.

Rotation of components on the gantry 212 and the operation of the x-ray source 214 are controlled by a control mechanism 226 of CT system 210. The control mechanism 226 includes an x-ray controller 228 that provides power and timing signals to the x-ray source 214 and a gantry motor controller 230 that controls the rotational speed and position of components on the gantry 212. A data acquisition system (DAS) 232 in the control mechanism 226 samples analog data from the detector elements 220 and converts the data to digital signals for subsequent processing. An image reconstructor 234 receives sampled and digitized x-ray data from the DAS 232 and performs high-speed image reconstruction. The reconstructed image is applied as an input to a computer 236 that stores the image in a storage device 238. The image reconstructor 234 can be specialized hardware or computer programs executing on the computer 236.

The computer 236 also receives commands and scanning parameters from an operator via a console 240 that has a keyboard and/or other user input and/or marking devices, such as a mouse, trackball, or light pen. An associated display 242, examples of which include a cathode ray tube (CRT) display, liquid crystal display (LCD), or plasma display, allows the operator to observe the reconstructed image and other data from the computer 236. The display 242 may include a user pointing device, such as a pressure-sensitive input screen. The operator supplied commands and parameters are used by the computer 236 to provide control signals and information to the DAS 232, x-ray controller 228, and gantry motor controller 230. In addition, the computer 236 operates a table motor controller 244 that controls a motorized table 246 to position the patient 222 in the gantry 212. For example, the table 246 moves portions of the patient 222 through a gantry opening 248.

In one embodiment, the computer 236 includes a device 250, for example, a floppy disk drive, CD-ROM drive, DVD drive, magnetic optical disk (MOD) device, or any other digital device including a network connecting device such as an Ethernet device for reading instructions and/or data from a computer-readable medium 252, such as a floppy disk, a CD-ROM, a DVD or another digital source such as a network or the Internet, as well as yet to be developed digital means. In another embodiment, the computer 236 executes instructions stored in firmware (not shown). The computer 236 is programmed to perform bone marrow segmentation methods described herein using a bone marrow segmentation module 260, which may be implemented in hardware, software or a combination thereof.

As used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. The CT system may be, for example, different types of CT imaging systems, such as a third generation CT system, a fourth generation CT system (stationary detector-rotating x-ray source) and a fifth generation CT system (stationary detector and x-ray source), as well as first and second generation CT systems. Additionally, it is contemplated that the benefits of the various embodiments accrue to imaging modalities other than CT. Further, although the herein described methods and apparatus are described in a medical setting, it is contemplated that the benefits of the various embodiments accrue to non-human imaging systems such as those systems typically employed in an animal imaging.

In operation, the CT system 210 acquires CT image data, for example, 3D volume imaged data of the patient that is used to generate bone marrow segmented images for display on the display 242.

Thus, various embodiments provide a 3D segmentation process for segmenting marrow in an imaged volume. Inaccuracies and partial volume effects causing marrow to appear joined or connected are avoided or reduced by practicing at least some of the various embodiments of the invention.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for identifying bone marrow in medical image data, the method comprising:
    obtaining a three-dimensional (3D) computed tomography (CT) volume data set corresponding to an imaged volume, the 3D CT volume data set acquired by a CT imaging system;
    identifying voxels in the 3D CT volume data set having a Hounsfield Unit (HU) value below a bone threshold, the voxels identified by one or more processors without using image continuity;
    marking the identified voxels as non-hone voxels and the non-identified voxels as bone voxels;
    determining, using the one or more processors, from the marked non-bone voxels, definite tissue voxels and non-definite tissue voxels, wherein determining includes identifying voxels surrounded by only marked non-bone voxels and connected, either directly or indirectly, to an initial voxel that is a marked non-bone voxel by other voxels that have been identified as definite tissue voxels, the identified voxels are marked as definite tissue voxels;
    expanding a region defined by the definite tissue voxels;
    masking the definite tissue voxels to remove the definite tissue voxels from the 3D CT volume data set; and
    identifying bone marrow from the non-definite tissue as un-masked voxels that are not the marked bone voxels.

2. A method in accordance with claim 1 wherein the expanding comprises adding at least one layer of voxels to the determined definite tissue voxels.

3. A method in accordance with claim 1 further comprising displaying an image of a 3D CT volume generated from the 3D CT volume data set and highlighting the voxels corresponding to the identified bone marrow.

4. A method in accordance with claim 1 further comprising dividing the voxels identified as bone marrow into red bone marrow and yellow bone marrow using corresponding red bone marrow HU values and yellow bone marrow HU values.

5. A method in accordance with claim 1 further comprising selecting as an initial voxel for the determining definite tissue voxels a non-bone voxel.

6. A method in accordance with claim 5 wherein the initial voxel is a corner voxel selected based on being not surrounded by the marked bone voxels in the 3D CT volume data set.

7. A method in accordance with claim 1 further comprising acquiring a full body CT scan of a patient to obtain the 3D CT volume data set.

8. A method in accordance with claim 1 further comprising determining a total mass of bone marrow based on the voxels corresponding to the identified bone marrow voxels.

9. A method in accordance with claim 1 wherein the bone threshold is 200 Hounsfield Units (HU).

10. A method in accordance with claim 1 wherein the bone threshold is determined based on an HU value for hard bone.

11. A method in accordance with claim 1 further comprising counting a number of neighbor marked non-bone voxels for each marked non-hone voxel, wherein the number represents a count value for each marked non-bone voxel;
    wherein the determining includes identifying definite voxels based on a count number of the non-bone voxel.

12. A method in accordance with claim 1 wherein the expanding comprises adding one or more layers of voxels adjacent to voxels that are marked non-bone voxels and are not determined definite tissue voxels.

13. A method in accordance with claim 1 wherein the definite tissue voxels comprise voxels identified as definitely not bone.

* * * * *